United States Patent [19]

Bobsein

[11] 4,430,515

[45] Feb. 7, 1984

[54] CATALYST COMPOSITIONS

[75] Inventor: Rex L. Bobsein, Bartlesville, Okla.

[73] Assignee: Phillips Petroleum Company, Bartlesville, Okla.

[21] Appl. No.: 415,201

[22] Filed: Sep. 7, 1982

[51] Int. Cl.$^3$ .............................................. C07C 2/10
[52] U.S. Cl. ...................................... 585/530; 585/18; 502/224
[58] Field of Search .................. 585/530, 18; 252/441

[56] References Cited

U.S. PATENT DOCUMENTS

| | | | |
|---|---|---|---|
| 2,382,586 | 8/1945 | Solomon et al. | 252/441 |
| 2,616,916 | 11/1952 | Heinrich | 585/530 |
| 3,068,306 | 12/1962 | Hay et al. | 585/18 |
| 3,082,196 | 3/1963 | D'Alelio | 252/442 |
| 3,149,178 | 9/1964 | Hamilton et al. | 585/18 |
| 3,156,736 | 11/1964 | Southern et al. | 585/18 |
| 3,303,239 | 2/1967 | Cleary et al. | 260/683.15 |
| 3,442,969 | 5/1969 | Banks | 260/683 |
| 3,773,853 | 11/1973 | Brennan et al. | 585/530 |
| 3,907,924 | 9/1975 | Isa et al. | 585/532 |
| 4,172,855 | 10/1979 | Shubkin et al. | 585/18 |
| 4,182,922 | 1/1980 | Schick | 585/18 |
| 4,282,392 | 8/1981 | Cupples et al. | 585/18 |
| 4,311,868 | 1/1982 | Ueno et al. | 585/530 |

*Primary Examiner*—Delbert E. Gantz
*Assistant Examiner*—Cynthia A. Prezlock

[57] ABSTRACT

The oligomerization of alpha-olefins to produce lube oil range oligomers is made more efficient with Group VB metal chlorides as catalysts.

5 Claims, No Drawings

CATALYST COMPOSITIONS

BACKGROUND

The oligomerization of hydrocarbons to produce synthetic lubricants has shown promise as an alternative to the current use of mineral oil lubricants. Synthetic lubricants will have molecular weights and other properties within defined limits so that their suitability for their intended uses can be assured.

THE INVENTION

The invention deals with the catalytic oligomerization of 1-olefins to produce oligomers, which oligomers have utility as lube oil components.

In one embodiment, 1-decene is polymerized in the presence of a catalyst containing tantalum chloride. The product contains a high percentage of $C_{30}$–$C_{40}$ oligomers.

ADVANTAGES

In accordance with the invention, the oligomerization of olefins can be effected with certain advantages. They include:

(1) high selectivity to $C_{30}$–$C_{40}$ oligomers, and
(2) high conversion of 1-decene to products.

OBJECTS OF THE INVENTION

It is one object of the invention to produce a composition which is useful as a catalyst for the oligomerization of olefins.

It is another object of the invention to make a catalyst composition which, when used to oligomerize olefins yields a high selectivity to highly desired oligomers.

It is still another object of the invention to carry out a process in which olefins are catalytically oligomerized to produce oligomers whose moledcular weights are within a desired range.

It is a further object of the invention to produce synthetic lubricants containing the oligomers produced using the catalyst composition and catalytic oligomerization process of the invention.

DESCRIPTION OF THE INVENTION

Catalyst

The catalyst of the invention contain at least one metal halide. Useful metal halides are chloride, fluorides, bromides, and iodides of Group VB metals. Chlorides are preferred.

The Group VB metals to be used herein include vanadium, niobium, and tantalum. Tantalum is preferred.

Mixtures of two or more halides, as well as mixtures of halides with other substances can be employed.

The use of other conventional catalyst components, e.g., carriers, is also contemplated.

Olefins

The monomers to be polymerized in accordance with the invention are mono- or polyunsaturated substances. Generally, they will contain between about 2 and 20 carbon atoms, with olefins having 6 to 16 carbon atoms preferred. 1-Decene is highly preferred. Mixtures of monomers can be used.

While the use of aliphatic olefins as reactants favors the production of long-chain polymers and oligomers there may be some branching present in the monomer reactant. The percentage of branching which is tolerable is generally any amount which will not be detrimental to either the polymerization of the monomer mixture or to the final properties of the polymers and oligomers which are desired.

Although the discussion above uses the term "monomers", the use of one or more low molecular weight polymerization products as reactants is contemplated.

Reaction Conditions

Oxygen and moisture must be excluded from the reactants. Solvent is necessary as a heat sink. The art is well aware of suitable parameters, such as temperature, time, etc., to be used in the polymerization of olefins. Accordingly, the following discussion is merely suggestive of possible guidelines for the artisan. Useful parameters depend to a large extent on the particular reactants and catalysts being employed.

Useful temperatures for the polymerization lie between about 50° C. and 200° C., with 90° C. to 160° C. preferred.

Useful reaction times range from 0.5 hrs. to 10 hrs., with 1 to 2 hrs. preferred.

Useful pressures range from 0.5 to 100 atmospheres, with 1 to 10 preferred.

Products

When the catalyst system of this invention is used, the polymerization of olefins produces a high yield of relatively low molecular weight molecules. In one embodiment, 1-decene is polymerized in the presence of tantalum chloride to produce a high percentage of $C_{30}$ to $C_{40}$ oligomers.

The utilities of the polymerizates made according to the invention depends upon the properties of the polymerized products. After hydrogenation the properties of $C_{30}$ to $C_{40}$ polymerizates make them suitable for use as lubricants. In addition to their use as synthetic lubricants, the products of the invention also have utility as waxes and as plasticizing agents for polymers.

EXAMPLE

To a 300 ml stainless steel autoclave fitted with magnetic stirrer, and argon purge were added 1.5 g $TaCl_5$, 18.0 g 1-decene and 75 mL heptane. The autoclave was sealed, flushed with argon and charged to 20 psig. A heater maintained reaction temperature at 149° C. After 2½ hours, the reactor was cooled to room temperature, the pressure vented and the reaction mixture removed. The catalyst was filtered off, and the filtrate was washed twice with 10% aqueous $NH_4OH$ (100 mL total), once with water and dried over 3 A molecular sieves. The heptane was removed on a rotary evaporator to yield reaction product.

84% of the decene was converted to oligomer with 55% of product as $C_{30}$ and $C_{40}$ (lube oil range) oligomers.

Analysis of product was by gas chromotography using a flame ionization detector.

Reasonable variations, such as would occur to the skilled artisan, can be made in the invention without departing from the scope thereof.

I claim:

1. A process of producing olefin polymers in which one or more $C_2$–$C_{20}$ olefin reactants are contacted with a catalyst consisting essentially of a tantalum halide under oligomerization conditions.

2. The process of claim 1 wherein the catalyst comprises tantalum chloride.

3. The process of claim 2 wherein the olefin reactant includes a $C_{6-16}$ alpha olefin.

4. The process of claim 3 wherein the olefin reactant is 1-decene.

5. The process of claim 4 wherein the catalyst is tantalum pentachloride.

* * * * *